US00PP37816P2

(12) United States Plant Patent
Yamada

(10) Patent No.: US PP37,816 P2
(45) Date of Patent: Oct. 20, 2026

(54) ***CALIBRACHOA* PLANT NAMED 'Suncal 0614'**

(50) Latin Name: ***Calibrachoa* sp.**
Varietal Denomination: Suncal 0614

(71) Applicant: Masahiro Yamada, Higashiomi (JP)

(72) Inventor: Masahiro Yamada, Higashiomi (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 19/342,139

(22) Filed: Sep. 26, 2025

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC . A01H 5/02; A01H 5/00; A01H 6/821; A01H 6/82
See application file for complete search history.

(56) References Cited

PUBLICATIONS

Suntory Flowers 2025 Suntory Flowers Variety View—Cast Countdown—3 New Faves, retrieved on Jan. 12, 2026 at https://suntoryflowers.com/2025/02/26/suntory-flowers-variety-view-cast-countdown-3-new-faves/, 5 pp. (Year: 2025).*
Suntory Flowers 2026 Catalog retrieved on Jan. 12, 2026 at https://suntoryflowers.com/catalog/, pp. 1-2, 56. (Year: 2026).*
Suntory Flowers Cast 2025 retrieved on Jan. 12, 2026 at https://suntoryflowers.com/cast2025/, 4 pp. (Year: 2026).*

* cited by examiner

*Primary Examiner* — June Hwu
(74) *Attorney, Agent, or Firm* — C. Anne Whealy

(57) ABSTRACT

A new and distinct cultivar of *Calibrachoa* plant named 'Suncal 0614', characterized by its upright to outwardly spreading and mounding plant habit; vigorous growth habit; freely branching habit; freely flowering habit; long flowering period; purple-colored flowers; and good garden performance.

2 Drawing Sheets

Figure 1:
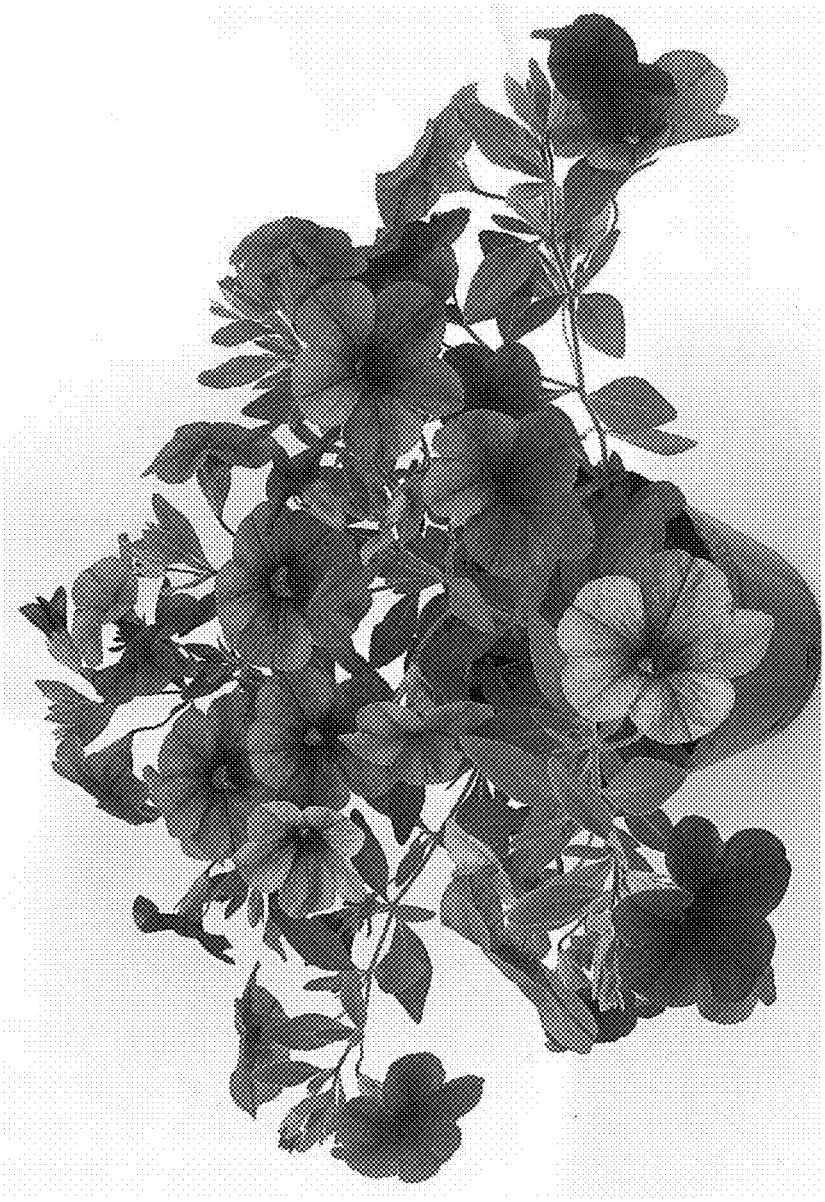

Botanical designation: *Calibrachoa* sp.
Cultivar denomination: 'SUNCAL 0614'.

BACKGROUND OF THE INVENTION

The present invention relates to a new and distinct cultivar of *Calibrachoa* plant, botanically known as *Calibrachoa* sp. and hereinafter referred to by the name 'Suncal 0614'.

The new *Calibrachoa* plant is a product of a planned breeding program conducted by the Inventor in Higashiomi, Shiga, Japan. The objective of the breeding program is to develop new mounding and freely branching *Calibrachoa* plants with numerous large purple-colored flowers.

The new *Calibrachoa* plant originated from a cross-pollination conducted by the Inventor in Higashiomi, Shiga, Japan in September 2017 of a proprietary selection of *Calibrachoa* sp. identified as code number CL16203-5, not patented, as the female, or seed, parent with a proprietary selection of *Calibrachoa* sp. identified as code number CL16204-2, not patented, as the male, or pollen, parent. The new *Calibrachoa* plant was discovered and selected by the Inventor as a single flowering plant from within the progeny of the stated cross-pollination in a controlled greenhouse environment in Higashiomi, Shiga, Japan in September 2018.

Asexual reproduction of the new *Calibrachoa* plant by terminal vegetative cuttings in a controlled greenhouse environment in Higashiomi, Shiga, Japan since March 2021 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncal 0614'. These characteristics in combination distinguish 'Suncal 0614' as a new and distinct *Calibrachoa* plant:

1. Upright to outwardly spreading and mounding plant habit.
2. Vigorous growth habit.
3. Freely branching habit.
4. Freely flowering habit.
5. Long flowering period.
6. Purple-colored flowers.
7. Good garden performance.

Plants of the new *Calibrachoa* can be compared to plants of the female parent selection. Plants of the new *Calibrachoa* differ primarily from plants of the female parent selection in flower color as plants of the new *Calibrachoa* have purple-colored flowers whereas plants of the female parent selection have rose-colored flowers.

Plants of the new *Calibrachoa* can be compared to plants of the male parent selection. Plants of the new *Calibrachoa* differ primarily from plants of the male parent selection in flower color as plants of the new *Calibrachoa* have purple-colored flowers whereas plants of the male parent selection have apricot-colored flowers.

Plants of the new *Calibrachoa* can also be compared to plants of *Calibrachoa* sp. 'Sunbel Kopachipi', disclosed in U.S. Plant Pat. No. 20,092. In side-by-side comparisons, plants of the new *Calibrachoa* and 'Sunbel Kopachipi' primarily differ in the following characteristics:

1. Plants of the new *Calibrachoa* are not as compact as plants of 'Sunbel Kopachipi'.
2. Plants of the new *Calibrachoa* have larger leaves than plants of 'Sunbel Kopachipi'.
3. Plants of the new *Calibrachoa* have larger flowers than plants of 'Sunbel Kopachipi'.
4. Flowers of plants of the new *Calibrachoa* are purple in color whereas flowers of plants of 'Sunbel Kopachipi' are reddish purple in color.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1) is a side perspective view of a typical flowering plant of 'Suncal 0614' grown in a container.

Figure 2:
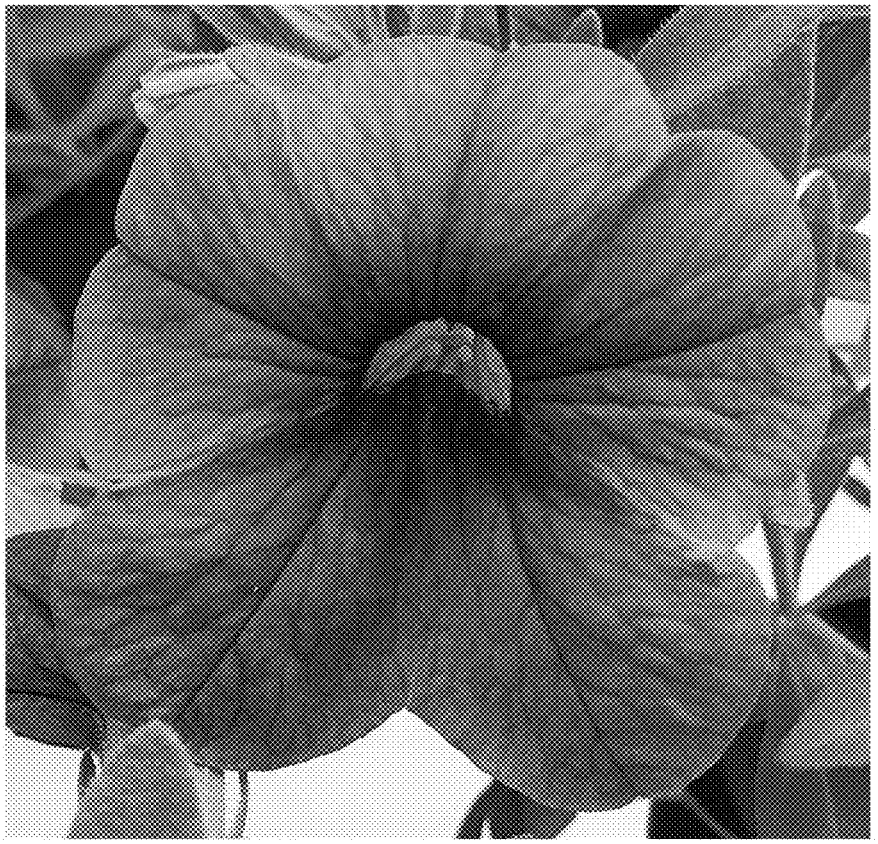

The photograph on the second sheet (FIG. 2) is a close-up view of a typical flower of 'Suncal 0614'.

DETAILED BOTANICAL DESCRIPTION

The aforementioned photographs and following observations, measurements and values describe plants grown during the early spring in 24-cm containers in an outdoor nursery in Higashiomi, Shiga, Japan and under cultural practices typical of commercial *Calibrachoa* production. During the production of the plants, day temperatures averaged 23° C. and night temperatures averaged 13° C. Plants were four months old when the photographs and the description were taken. In the following description, color references are made to The Royal Horticultural Society Colour Chart, 2015 Edition, except where general terms of ordinary dictionary significance are used.

Botanical classification: *Calibrachoa* sp. 'Suncal 0614'.

Parentage:

*Female, or seed, parent.*—Proprietary selection of *Calibrachoa* sp. identified as code number CL16203-5, not patented.

*Male, or pollen, parent.*—Proprietary selection of *Calibrachoa* sp. identified as code number CL16204-2, not patented.

Propagation:

*Type.*—By vegetative terminal cuttings.

*Time to initiate roots, summer and winter.*—About one week at temperatures about 15° C. to 20° C.

*Time to produce a rooted young plant, summer and winter.*—About three weeks at temperatures about 15° C. to 20° C.

*Root description.*—Fibrous; typically white in color; actual color of the roots is dependent on substrate composition, water quality, fertilizer type and formulation, substrate temperature and physiological age of roots.

*Rooting habit.*—Freely branching.

Plant description:

*Plant and growth habit.*—Upright to outwardly spreading and mounding plant habit; freely branching habit with numerous lateral branches developing per plant; pinching enhances lateral branch development; vigorous growth habit.

*Plant height.*—About 17.2 cm.

*Plant diameter.*—About 32.4 cm.

Lateral branch description:

*Length.*—About 17.8 cm.

*Diameter.*—About 1.6 mm.

*Internode length.*—About 2.2 cm.

*Strength.*—Strong.

*Aspect.*—Upright to somewhat outwardly.

*Texture.*—Densely pubescent; rough.

*Color.*—Close to 138B.

Leaf description:

*Arrangement and quantity.*—Alternate, simple; about 17 leaves per lateral branch.

*Length.*—About 4.5 cm.

*Width.*—About 1.9 mm.

*Shape.*—Ovate.

*Apex.*—Obtuse.

*Base.*—Attenuate.

*Margin.* Entire.

*Texture, upper and lower surfaces.*—Densely pubescent; rough.

*Venation pattern.*—Pinnate; reticulate.

*Color.*—Developing leaves, upper surface: Close to 137C. Developing leaves, lower surface: Close to 138B. Fully expanded leaves, upper surface: Close to 137B; venation, close to 138B. Fully expanded leaves, lower surface: Close to 138B; venation, close to 138C.

*Petioles.*—Length: About 6.8 mm. Diameter: About 2.4 mm. Texture, upper and lower surfaces: Pubescent; rough. Color, upper and lower surfaces: Close to 137B.

Flower description:

*Flower arrangement and habit.*—Single salverform flowers arising from upper leaf axils; freely flowering habit with usually about 41 flowers developing per plant; flowers face mostly upright to outwardly.

*Fragrance.*—None detected.

*Natural flowering season.*—Early flowering habit, plants of the new *Calibrachoa* initiate and develop flowers about three to four weeks after planting; long flowering period, flowering naturally commences during the spring and plants flower continuously throughout the summer into the late autumn in Japan.

*Flower longevity.*—Individual flowers last about seven to ten days on the plant; flowers not persistent.

*Flower buds.*—Length: About 2.8 cm. Diameter: About 8.5 mm. Shape: Cylindrical. Color: Distally, close to N77B; proximally, close to 151D; venation, close to N77A.

*Flower diameter.*—About 4.8 cm.

*Flower length (depth).*—About 1.4 cm.

*Tube length.*—About 1.8 cm.

*Tube diameter, distally.*—About 8.8 mm.

*Tube diameter, proximally.*—About 2.3 mm.

*Corolla.*—Arrangement: Five petals fused at the base and opening into a flared trumpet. Petal length from throat: About 2 cm. Petal width: About 2.3 cm. Petal shape: Roughly spatulate. Petal apex: Rounded, blunt; slightly retuse. Petal margin: Entire; slightly undulate. Petal texture, upper and lower surfaces: Smooth, glabrous. Throat texture: Pubescent. Tube texture: Smooth, glabrous. Color: Petal, when opening, upper surface: Close to N81A. Petal, when opening, lower surface: Close to N80B. Petal, fully opened, upper surface: Close to N81B; venation, close to N81B; color becoming closer to N81D with subsequent development. Petal, fully opened, lower surface: Close to N80C; color does not change with subsequent development. Throat: Close to 7A; venation, close to 7A. Tube: Close to 7B; venation, close to N79C.

*Calyx.*—Arrangement: Star-shaped tubular calyx tube with five sepals in a single whorl and fused at the base. Sepal length: About 1.2 cm. Sepal width: About 3.2 mm. Sepal shape: Lanceolate. Sepal apex: Obtuse. Sepal margin: Entire. Sepal texture, upper and lower surfaces: Pubescent; rough. Sepal color, upper and lower surfaces: Close to 138B.

*Peduncles.*—Length: About 2.5 cm. Diameter: About 1 mm. Angle: Upright to outwardly. Strength: Strong. Texture: Pubescent; rough. Color: Close to 144A.

*Reproductive organs.*—Stamens: Quantity: Five per flower. Filament length: About 8.8 mm. Filament color: Close to 145D. Anther shape: Ellipsoidal. Anther size: About 1.3 mm by 1.8 mm. Anther color: Close to 2D. Pollen amount: Moderate. Pollen color: Close to 2D. Pistils: Quantity: One per flower. Pistil length: About 1.1 cm. Style color: Close to 145B. Stigma shape: Transversely ellipsoidal. Stigma color: Close to 145A. Ovary color: Close to 145A.

*Seeds and fruits.*—To date, seed and fruit development have not been observed on plants of the new *Calibrachoa.*

Garden performance: Plants of the new *Calibrachoa* have been observed to have good garden performance and to tolerate wind, rain and temperatures ranging from about 5° C. to about 35° C.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'Suncal 0614' as herein illustrated and described.

* * * * *